United States Patent
Jeng et al.

(10) Patent No.: US 9,554,882 B2
(45) Date of Patent: Jan. 31, 2017

(54) METHOD OF MAKING CALCIUM-FLUORIDE LAYER FORMED ON AN OBJECT SURFACE FOR MORE WEAR RESISTANCE

(71) Applicant: NATIONAL CHUNG CHENG UNIVERSITY, Chia-Yi County (TW)

(72) Inventors: Yeau-Ren Jeng, Tainan (TW); Tsung-Ting Lin, Chiayi (TW); Yu-Xian Huang, Tainan (TW); Dar-Bin Shieh, Tainan (TW)

(73) Assignee: NATIONAL CHUNG CHENG UNIVERSITY, Chia-Yi County (TW)

( * ) Notice: Subject to any disclaimer, the term of this patent is extended or adjusted under 35 U.S.C. 154(b) by 187 days.

(21) Appl. No.: 14/542,072

(22) Filed: Nov. 14, 2014

(65) Prior Publication Data

US 2016/0135937 A1 May 19, 2016

(51) Int. Cl.
*A61C 5/00* (2006.01)
*A61C 19/06* (2006.01)
*A61K 6/00* (2006.01)

(52) U.S. Cl.
CPC ........... *A61C 19/063* (2013.01); *A61K 6/0017* (2013.01)

(58) Field of Classification Search
CPC ... A61C 19/003; A61C 19/063; A61C 1/0046; A61K 6/0017
See application file for complete search history.

(56) References Cited

U.S. PATENT DOCUMENTS

| 6,104,853 A * | 8/2000 | Miyagi | A61B 18/22 385/125 |
| 2014/0162208 A1* | 6/2014 | Stookey | A61K 8/21 433/82 |
| 2014/0242535 A1* | 8/2014 | Lowe | A61C 19/063 433/18 |

* cited by examiner

*Primary Examiner* — George Manuel
(74) *Attorney, Agent, or Firm* — Muncy, Geissler, Olds & Lowe, P.C.

(57) ABSTRACT

A method of making a calcium-fluoride layer formed on an object surface for more wear resistance includes the steps of coating sodium fluoride to a surface of an object having calcium, whereby the calcium fluoride and the calcium are inverted to become a calcium-fluoride layer on the surface of the object after a chemistry reaction; preparing a $CO_2$ laser device having a $CO_2$ laser emitter for emitting $CO_2$ laser; and applying irradiation of the $CO_2$ laser via the $CO_2$ laser emitter to the calcium-fluoride layer for at least five seconds. In light of this, the wear resistance of the calcium-fluoride layer is enhanced for at least 34%, the absorption rate of the fluoride is increased for at least 23%, and the surface of the object has aesthetic and integral appearance.

10 Claims, 6 Drawing Sheets

--- a. Coat sodium fluoride to a surface of an object having calcium. A calcium-fluoride layer is formed on the surface of the object.

b. Prepare a CO2 laser device having a CO2 laser emitter.

c. Apply irradiation of the CO2 laser via the CO2 laser emitter to the calcium-fluoride layer on the object for at least five seconds.

METHOD OF MAKING CALCIUM-FLUORIDE LAYER FORMED ON AN OBJECT SURFACE FOR MORE WEAR RESISTANCE

BACKGROUND OF THE INVENTION

1. Field of the Invention

The present invention relates generally to wear resistance of an object and more particularly, to a method of making a calcium-fluoride layer formed on an object surface for more wear resistance.

2. Description of the Related Art

Fluoride is a natural element and exists in many common eatable foods, such as tea, taros, seafood, and drinking water. Fluorine has high affinity for calcium and can invert calcium hydroxyapatite of dental enamels into calcium fluoroapatite having lower solubility to further reduce the solubility of the dental enamels in an acid. Fluorine can also be linked up with calcium ionized by the acid to jointly return to the dental enamels, as known as remineralization.

The aforesaid conventional way of increasing the wear resistance of an object is to coat fluoride to a part of the object. However, the calcium-fluoride layer on the surface of the object is soft and has poor wear resistance, so it is necessary to frequently coat the fluoride to the object. Besides, after the calcium-fluoride layer suffers wear and tear, the surface of the object becomes inaesthetic.

SUMMARY OF THE INVENTION

The primary objective of the present invention is to provide a method of making a calcium-fluoride layer formed on an object surface for more wear resistance. The method includes a step of applying laser irradiation to a calcium-fluoride layer of the object surface to increase both of the wear resistance of the calcium-fluoride layer and the absorption of the fluoride for aesthetic and integral appearance of the object.

The foregoing objective of the present invention is attained by the method having the steps of coating sodium fluoride to a surface of an object having calcium, whereby the calcium fluoride and the calcium are inverted to become a calcium-fluoride layer on the surface of the object after a chemistry reaction; preparing a laser device having a laser emitter for emitting a laser; and applying irradiation of the laser via the laser emitter to the calcium-fluoride layer for at least five seconds.

DETAILED DESCRIPTION OF PREFERRED EMBODIMENTS

Figure 1:
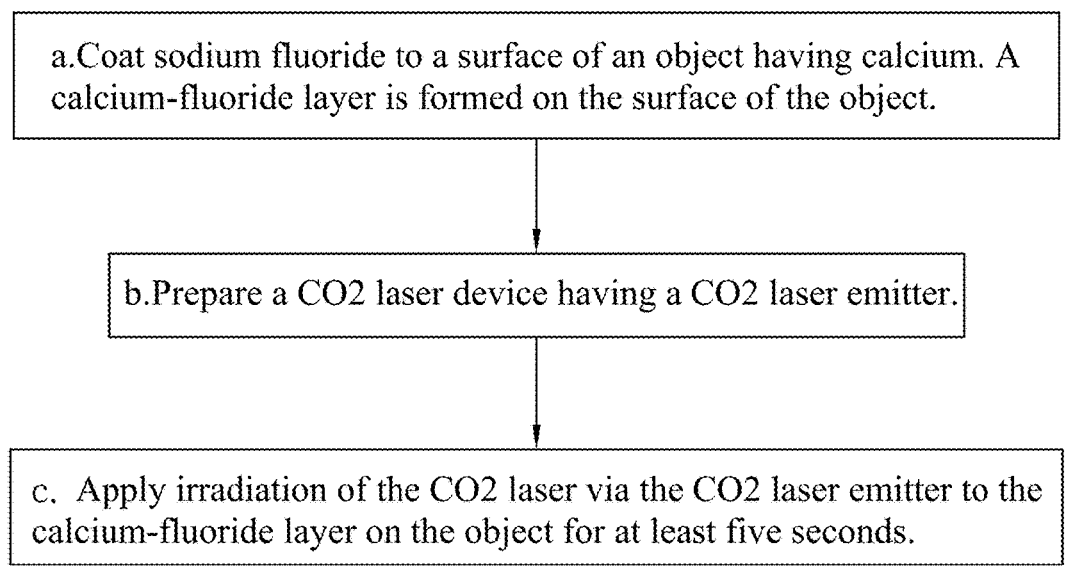
FIG. 1 is a flow chart for first and second preferred embodiments of the present invention.

Referring to FIG. 1, a method of making a calcium-fluoride layer formed on an object surface for more wear resistance in accordance with a first preferred embodiment of the present invention includes the following steps.

a) Coat sodium fluoride to a surface of an object having calcium. After a chemistry reaction, the sodium fluoride and the calcium are inverted become a calcium-fluoride layer on the surface of the object.

b) Prepare a carbon dioxide ($CO_2$) laser device (not shown) having a $CO_2$ laser emitter (not shown) for emitting $CO_2$ laser. In this preferred embodiment, the $CO_2$ laser device further includes a programmable logic controller (PLC) (not shown), a three-axis mechanical arm (not shown), a charge-coupled device (CCD) camera lens (not shown), a data processing device (not shown), and a display (not shown). The PLC, the three-axis mechanical arm, the CCD camera lens, the data processing device, and the display are electrically connected with one another. The $CO_2$ laser emitter and the CCD camera lens are fixed to the Z-axis of the three-axis mechanical arm. The three-axis mechanical arm is controlled by the PLC. The CCD camera lens can capture an image of the object and immediately transmit it to the data processing device, such as computer, and after the image is processed, a positioning control based on laser dotting is applied onto the display.

c) Apply irradiation of the $CO_2$ laser via the $CO_2$ laser emitter to the calcium-fluoride layer on the object for at least five seconds. In this way, the wear resistance of the calcium-fluoride layer can be enhanced and the absorption rate of the fluoride can be increased. In this preferred embodiment, as indicated in Table 1 shown below, experiments of hardness, Elastic Modulus, and mean wear depth are applied to 2% fluoride not irradiated by the $CO_2$ laser, 2% fluoride irradiated by the $CO_2$ laser for five seconds, and 2% fluoride irradiated by the $CO_2$ laser for ten seconds.

TABLE 1

Enamel Surface Treatment

|  | 2% NaF | 2% (NaF + L5 s) | 2% (NaF + L10 s) |
|---|---|---|---|
| Hardness (GPa) | 0.79 ± 0.18 | 1.76 ± 0.37 | 1.99 ± 0.56 |
| Elastic Modulus (GPa) | 43.79 ± 5.68 | 59.72 ± 21.40 | 53.32 ± 22.53 |
| Mean Wear Depth (nm) |  |  |  |
| 300 μN | 28.1 ± 2.6 | 14.7 ± 1.4 | 12.8 ± 2.6 |
| 350 μN | 30.6 ± 1.1 | 17.1 ± 1.3 | 16.7 ± 3.1 |
| 400 μN | 35.49 ± 4.8 | 23.5 ± 3.2 | 21.6 ± 1.6 |

Note:
GPa ($10^9$ Pa; 1 Pa = 1 $N/m^2$ as a pressure unit), μN ($10^{-6}$ N as a strength unit), and nm ($10^{-9}$ m as a length unit).

Figure 2:
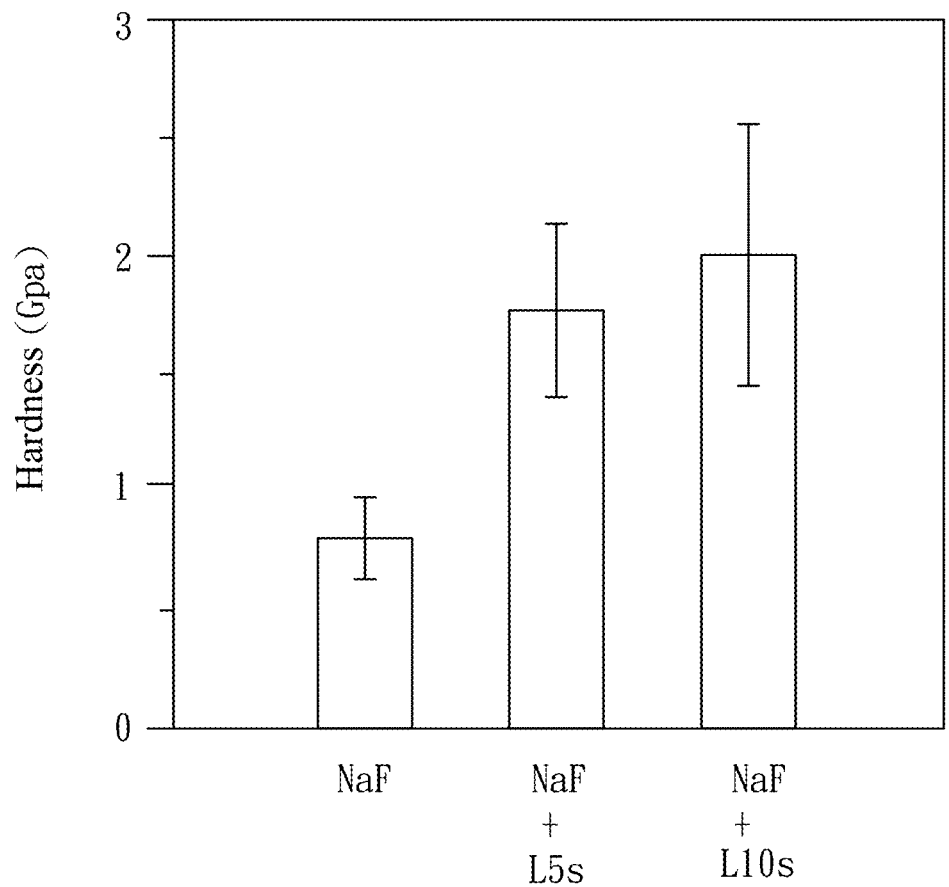
FIG. 2 shows results of experiments on hardness in accordance with the first and second preferred embodiments of the present invention.

Referring to FIG. 2 showing a histogram of experiments on hardness, in view of the experimental data indicated in Table 1, the sodium fluoride is coated onto the surface of the object having the calcium and then the sodium fluoride and the calcium are inverted to become the calcium-fluoride layer on the surface of the object after the chemical reaction. When the $CO_2$ laser is not irradiated on the calcium-fluoride layer, the hardness of the calcium-fluoride layer is 0.76±0.18 GPa. When the $CO_2$ laser is irradiated on the calcium-fluoride layer for five seconds, the hardness of the calcium-fluoride layer is 1.76±0.37 GPa, leading to a hardness enhancement rate of 123% [(1.76−0.79)/0.79%]. When the $CO_2$ laser irradiates on the calcium-fluoride layer for ten seconds, the hardness of the calcium-fluoride layer is 1.99±0.56 GPa, leading to a hardness enhancement rate of 152% [(1.99−0.79)10.79%].

Figure 3:
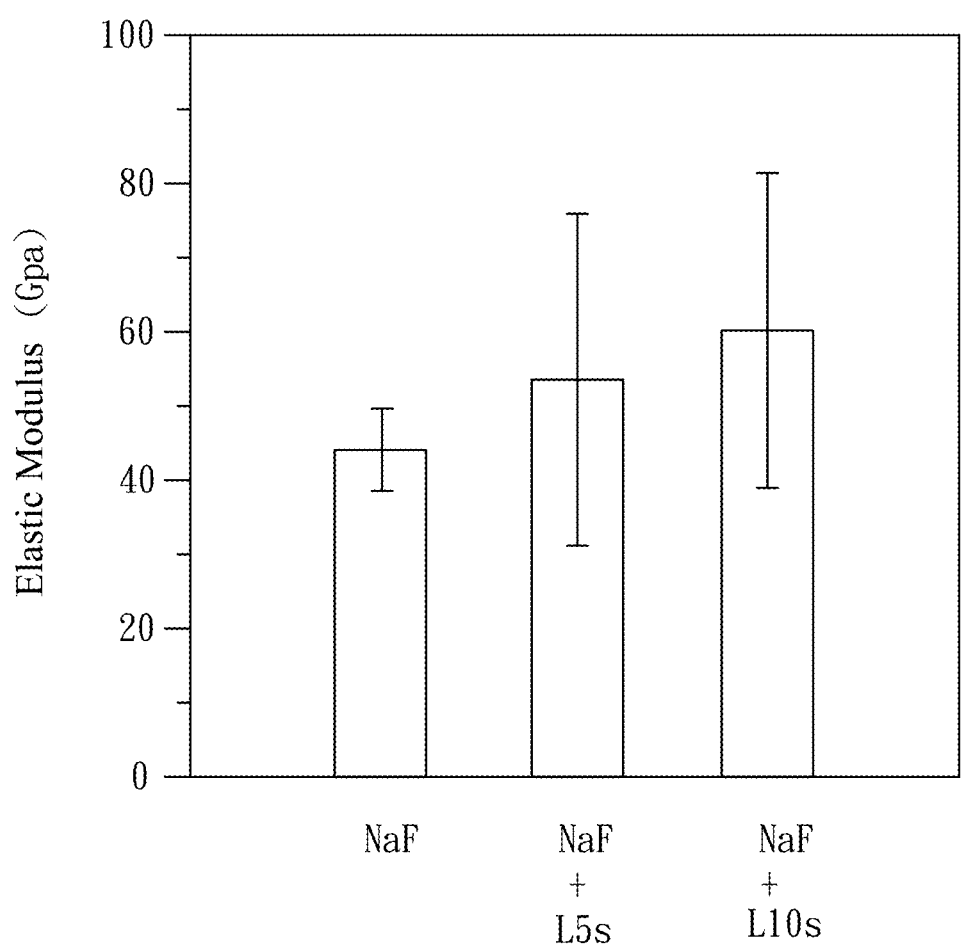
FIG. 3 shows results of experiments based on Elastic Modulus in accordance with the first and second preferred embodiments of the present invention.

Referring to FIG. 3 and in view of Table 1, the sodium fluoride is coated to the surface of the object having the calcium and after the chemical reaction, the sodium fluoride and the calcium are inverted to become the calcium-fluoride layer. Before the calcium-fluoride layer is irradiated by the $CO_2$ laser, Elastic Modulus of the calcium-fluoride layer is 43.79±5.68 GPa. When the calcium-fluoride layer is irradiated by the $CO_2$ laser for five seconds, Elastic Modulus of the calcium-fluoride layer becomes 59.72±21.40 GPa for 36% [(59.72−43.79)143.79] enhancement. When the calcium-fluoride layer is irradiated by the $CO_2$ laser for ten seconds, Elastic Modulus of the calcium-fluoride layer becomes 53.32±22.53 GPa for 22% [(53.32−43.79)/43.79] enhancement.

Figure 4:
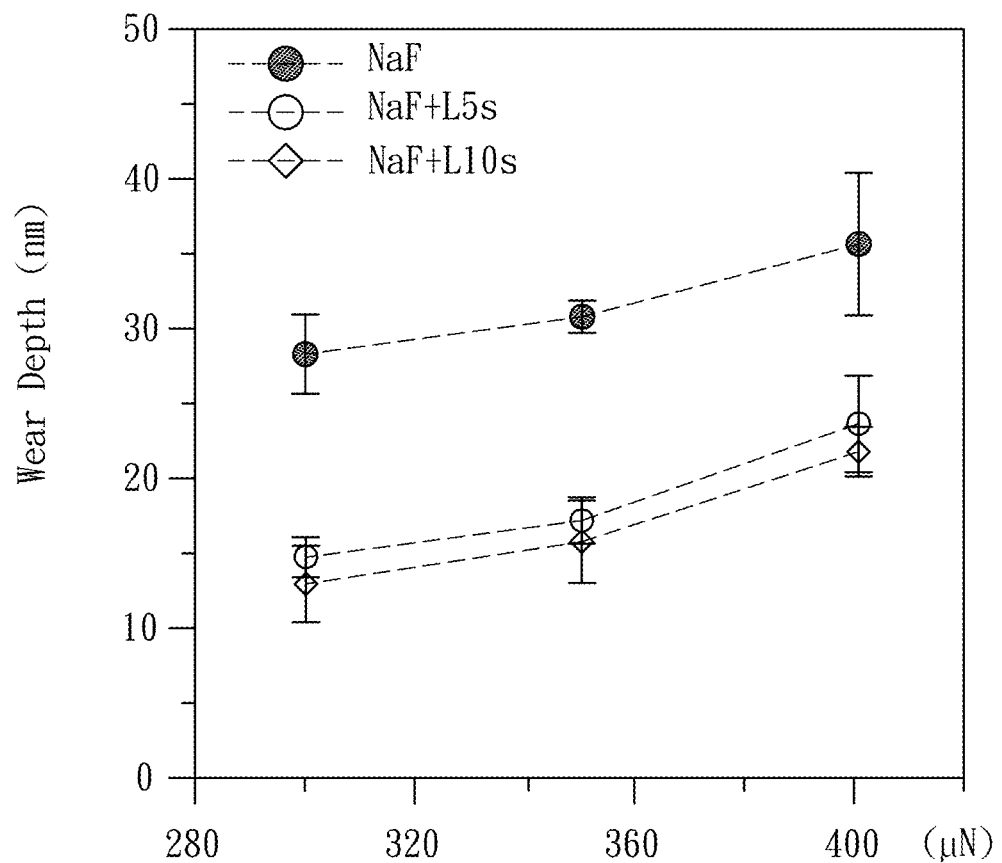
FIG. 4 shows results of experiments on wear depth in accordance with the first and second preferred embodiments of the present invention.

Referring to FIG. 4 and in view of Table 1, the sodium fluoride is coated to the surface of the object having calcium, and after the chemical reaction, the sodium fluoride and the calcium are inverted to become the calcium-fluoride layer. Before the calcium-fluoride layer is irradiated by the $CO_2$ laser, the mean wear depth of the surface of the object with the calcium-fluoride layer under the force of 400 μN is 35.49±4.8 nm. When the calcium-fluoride layer is irradiated by the $CO_2$ laser for five seconds, the mean wear depth of the surface of the object with the calcium-fluoride layer under the force of 400 μN becomes 23.5±3.2 nm, so the wear resistance is 34% [(35.49−23.5)135.49] for 34% enhancement. When the calcium-fluoride layer is irradiated by the $CO_2$ laser for ten seconds, the mean wear depth of the surface of the object with the calcium-fluoride layer under the force of 400 μN becomes 35.49±4.8 nm, so the wear resistance is 40% [(35.49−23.5)/35.49] for 40% enhancement.

As known from the experiments indicated above, after processed by the $CO_2$ laser, the calcium-fluoride layer becomes compact in texture due to mass transfer, so the hardness and Elastic Modulus are greatly enhanced and meanwhile, the wear resistance is also enhanced, as shown in FIGS. 2 and 3; namely, the wear resistance is enhanced for 34% when the $CO_2$ laser irradiates the calcium-fluoride layer for five seconds; the wear resistance is enhanced for 40% when the $CO_2$ laser irradiates the calcium-fluoride layer for ten seconds.

Figure 5:
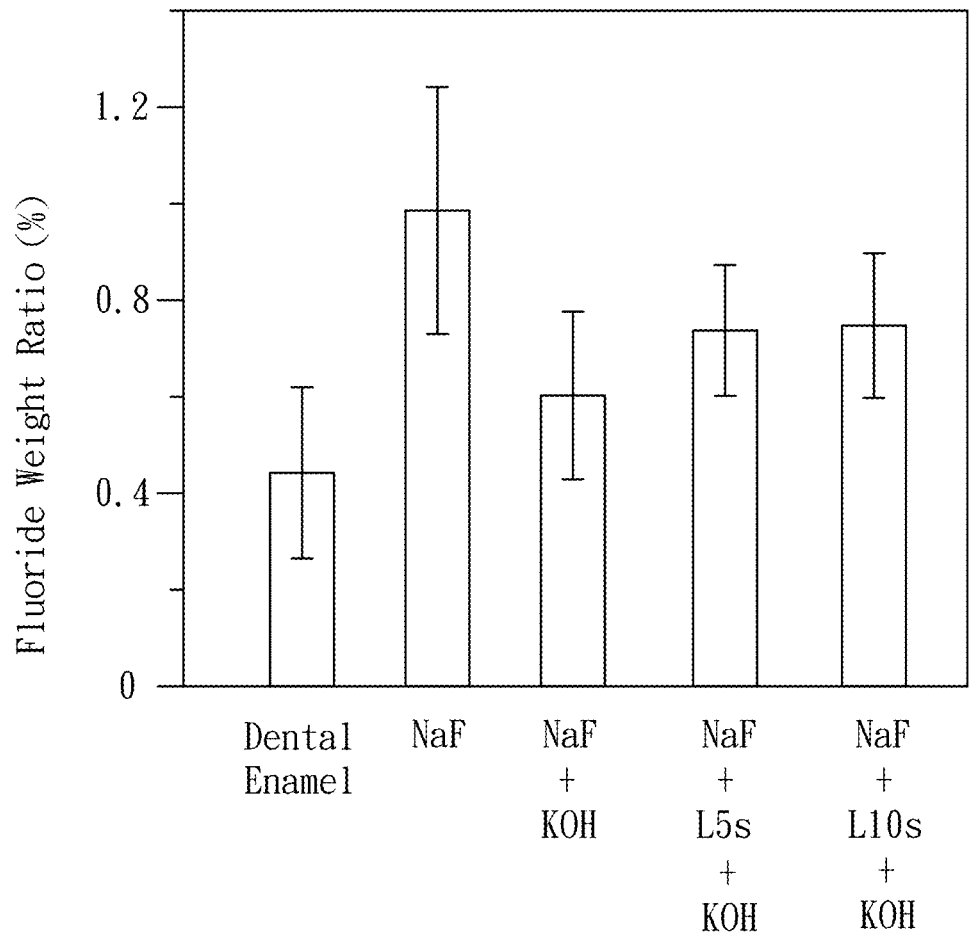
FIG. 5 shows result of experiments on residue of fluoride in accordance with the first and second preferred embodiments of the present invention.

Referring to FIG. 5 and in view of Table 2 indicated below, after processed by the coating of the sodium fluoride, the surface of the object is inverted to form the calcium-fluoride layer thereon after the chemical reaction and next, potassium hydroxide (KOH) is used to remove the sodium fluoride on the surface of the object; meanwhile, the detected fluoride residue is 0.6010.17 wt % as referred to (NaF+KOH) in FIG. 5. After processed by the coating of the sodium fluoride, the sodium fluoride and the calcium are inverted to become the calcium-fluoride layer on the surface of the object after the chemical reaction and then, the $CO_2$ laser irradiates the calcium-fluoride layer for five seconds to make calcium-fluoride crystals dissolved into the object or into dental enamel; soon the KOH is used to remove the sodium fluoride on the surface of the object; meanwhile, it is found that the fluoride residue is 0.7410.14 wt % and the enhancement rate of the fluoride residue is 23% [(0.74−0.60) 10.60] as referred to NaF+L5s+KOH in FIG. 5. After processed by the coating of the sodium fluoride, the surface of the object is irradiated by the $CO_2$ laser for ten seconds to make the calcium-fluoride crystals dissolved into the object or the dental enamel and soon the KOH is used to remove sodium fluoride on the surface of the object; meanwhile, it is found that the fluoride residue is 0.7410.15 wt % and the enhancement rate of the fluoride residue is 23% [(0.74−0.60)/0.60] as referred to NaF+L10s+KOH in FIG. 5.

TABLE 2

|  | En | NaF | NaF + KOH | NaF + L5 S + KOH | NaF + L10 S + KOH |
|---|---|---|---|---|---|
| Fluoride Weight Ratio (wt %) | 0.44 ± 0.18 | 0.99 ± 0.26 | 0.60 ± 0.17 | 0.74 ± 0.14 | 0.74 ± 0.15 |

As known from the experimental results mentioned above, when the irradiation of the $CO_2$ laser lasts for at least five seconds, the fluoride residue is enhanced for at least 23%. Further, the enhancement rate of the fluoride residue is actually identical to the absorption rate of the fluoride on the object.

Figure 6A:
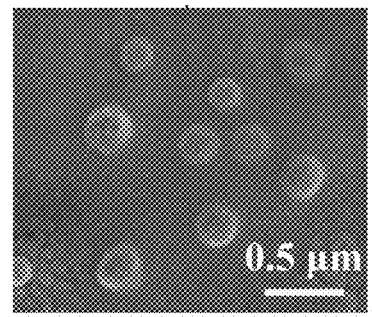
FIG. 6a is an electromicroscopic photo of the fluoride without irradiation of $CO_2$ laser in accordance with the first and second preferred embodiments of the present invention, showing that the number of calcium-fluoride-like crystals on a fluorine-coated area.
Figure 6B:
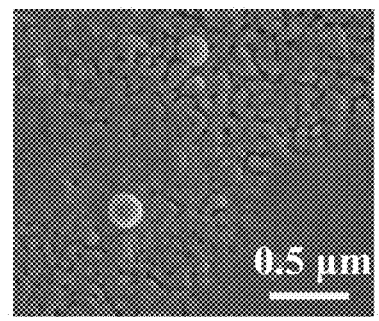
FIG. 6b is an electromicroscopic photo of the fluoride irradiated by the $CO_2$ laser for five seconds in accordance with the first and second preferred embodiments of the present invention, showing that the number of the calcium-fluoride-like crystals on the fluorine-coated area.
Figure 6C:
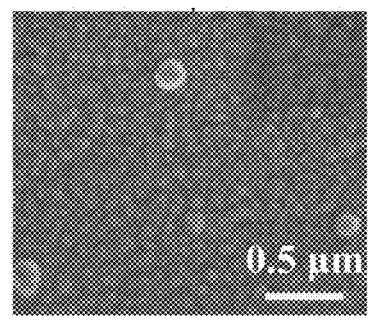
FIG. 6c is an electromicroscopic photo of fluoride irradiated by the $CO_2$ laser for ten seconds in accordance with the first and second preferred embodiments of the present invention, showing that the number of the calcium-fluoride-like crystals on the fluorine-coated area.

Referring to FIG. 6a showing an electromicroscopic photo (×130000), there are nine $CaF_2$-like crystals having the diameter of 240.20±27.62 nm at a fluoride-coated area of 1 $\mu m^2$. Referring to FIG. 6b showing an electromicroscopic photo (×130000), the sodium fluoride is irradiated by the $CO_2$ laser for five seconds, so there are one or two $CaF_2$-like crystals having the diameter of 192.12±26.39nm at the fluoride-coated area of 1 $\mu m^2$. Referring to FIG. 6c showing an electromicroscopic photo (×130000), the sodium fluoride is irradiated by the $CO_2$ laser for ten seconds, so there are one or two $CaF_2$-like crystals having the diameter of 138.06±27.55nm at the fluoride-coated area of 1 $\mu m^2$. In light of this, the $CO_2$ laser will make the diameter of the $CaF_2$-like crystals become small or even melt the $CaF_2$-like crystals.

In light of the aforesaid experiments, when the calcium fluoride is irradiated by the $CO_2$ laser for five or ten seconds, the enhancement rate of the fluoride residue reaches at least 23% as shown in FIGS. 5, 6*a*, 6*b*, and 6*c*.

Referring to FIGS. 1-6*c*, a method of making a calcium-fluoride layer formed on a dental surface for more wear resistance in accordance with a second preferred embodiment of the present invention is similar to that of the first preferred embodiment, having the difference lying in that the object mentioned in the first preferred embodiment is changed to a plurality of teeth in the second preferred embodiment.

Since the other content including the effects attained by the steps of the second preferred embodiment are identical to those of the first preferred embodiment, more recitation of the same is skipped.

In the aforesaid first and second preferred embodiments of the present invention, the $CO_2$ laser device can be either of other general laser devices as long as it can achieve the same effect.

In conclusion, the present invention can solve the problems that it is necessary to frequently coat fluoride onto the object because the calcium fluoride on the surface of the object is less hard and has poor wear resistance and it leads to inaesthetic appearance. After the sodium fluoride is coated to the surface of the object, the $CO_2$ laser irradiates the calcium-fluoride layer on the object to enhance the wear resistance of the calcium-fluoride layer and the absorption of the fluoride, so the surface of the object in the present invention has aesthetic and integral appearance.

What is claimed is:

1. A method of making a calcium-fluoride layer formed on an object surface for more wear resistance, comprising steps of:
    coating sodium fluoride to a surface of an object having calcium, whereby after a chemical reaction, the sodium fluoride and the calcium are inverted to become a calcium-fluoride layer on the surface of the object;
    preparing a laser device having a laser emitter for emitting laser; and
    applying irradiation of the laser to the calcium-fluoride layer via the laser emitter for at least five seconds, whereby the wear resistance of the calcium-fluoride layer is enhanced and absorption of the fluoride on the object is increased;
    wherein in the second step, the laser device further comprises a programmable logic controller (PLC), a three-axis mechanical arm, a charge-coupled device (CCD) camera lens, a data processing device, and a display, all of which are electrically connected with one another, the laser emitter and the CCD camera lens being fixed to the Z-axis of the three-axis mechanical arm, the three-axis mechanical arm being controlled by the PLC, whereby the CCD camera lens captures an image of the object and immediately transmits it to the data processing device, and after the image is processed, a positioning control based on laser dotting is applied onto the display.

2. The method as defined in claim 1, wherein the laser device is a carbon dioxide ($CO_2$) laser device.

3. The method as defined in claim 1, wherein the calcium-fluoride layer is irradiated by the laser for five seconds to enhance its wear resistance for at least 34%.

4. The method as defined in claim 1, wherein the calcium-fluoride layer is irradiated by the laser for ten seconds to enhance its wear resistance for at least 40%.

5. The method as defined in claim 1, wherein the object is irradiated by the laser for at least five seconds to enhance its absorption of the fluoride for at least 23%.

6. A method of making a calcium-fluoride layer formed on a dental surface for more wear resistance, comprising steps of:
    coating sodium fluoride to surfaces of teeth having calcium, whereby after a chemical reaction, the sodium fluoride and the calcium are inverted to become a calcium-fluoride layer on the surfaces of the teeth;
    preparing a laser device having a laser emitter for emitting laser; and
    applying irradiation of the laser to the calcium-fluoride layer via the laser emitter for at least five seconds, whereby the wear resistance of the calcium-fluoride layer is enhanced and absorption of the fluoride on the teeth is increased;
    wherein in the second step, the laser device further comprises a PLC, a three-axis mechanical arm a CCD camera lens, a data processing device, and a display, all of which are electrically connected with one another, the laser emitter and the CCD camera lens being fixed to the Z-axis of the three-axis mechanical arm, the three-axis mechanical arm being controlled by the PLC, whereby the CCD camera lens captures an image of the teeth and immediately transmits it to the data processing device, and after the image is processed, a positioning control based on laser dotting is applied onto the display.

7. The method as defined in claim 6, wherein the laser device is a $CO_2$ laser device.

8. The method as defined in claim 6, wherein the calcium-fluoride layer is irradiated by the laser for five seconds to enhance its wear resistance for at least 34%.

9. The method as defined in claim 6, wherein the calcium-fluoride layer is irradiated by the laser for ten seconds to enhance its wear resistance for at least 40%.

10. The method as defined in claim 6, wherein the object is irradiated by the laser for at least five seconds to enhance its absorption of the fluoride for at least 23%.

* * * * *